United States Patent [19]
Bachtler et al.

[11] Patent Number: 5,824,834
[45] Date of Patent: *Oct. 20, 1998

[54] PROCESS FOR THE PRODUCTION OF ACETYLENE AND SYNTHESIS GAS

[75] Inventors: Michael Bachtler, Neustadt, Germany; Rudolf R. Schnur, Baton Rouge, La.; Peter Pässler, Ludwigshafen, Germany; Olaf Scheidsteger, Mannheim, Germany; Werner Kastenhuber, Mutterstadt, Germany; Gerd Schlindwein, Ludwigshafen, Germany; Rainer König, Kallstadt, Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 543,879

[22] Filed: Oct. 19, 1995

[51] Int. Cl.$^6$ .................................................. C07C 2/78
[52] U.S. Cl. .................... 585/540; 585/537; 585/538; 585/921; 585/922
[58] Field of Search .................. 582/534, 538, 582/540, 541, 921, 922, 537

[56] References Cited

U.S. PATENT DOCUMENTS

| | | | |
|---|---|---|---|
| 2,503,188 | 4/1950 | Bergstom | 585/921 |
| 2,679,542 | 5/1954 | Dorsey | 585/541 |
| 2,692,902 | 10/1954 | Pichler et al. | 585/541 |
| 2,721,227 | 10/1955 | Mungen | 585/541 |
| 2,765,359 | 10/1956 | Pichler et al. | 260/679 |
| 2,816,942 | 12/1957 | Bills | 585/541 |
| 2,966,533 | 12/1960 | Alstaedt et al. | 585/541 |
| 2,998,464 | 8/1961 | Burleson et al. | 585/921 |
| 3,292,913 | 12/1966 | Craig | 585/921 |
| 3,399,245 | 8/1968 | Knapp | 585/540 |
| 3,485,590 | 12/1969 | Loeffler, Jr. | 585/921 |
| 4,575,383 | 3/1986 | Lowther et al. | 48/212 |
| 4,767,569 | 8/1988 | Brophy et al. | 252/373 |
| 4,952,743 | 8/1990 | Come | 585/541 |
| 5,015,799 | 5/1991 | Walker et al. | 585/500 |

FOREIGN PATENT DOCUMENTS

| | | |
|---|---|---|
| 378 083 | 7/1990 | European Pat. Off. . |
| 1319326 | 1/1962 | France . |
| 1259875 | 7/1960 | Germany . |

OTHER PUBLICATIONS

H. Pichler, *Chemical Engineering Progress*, vol. 61, No. 8, pp. 63–67, "Acetylene from hydrocarbon–oxygen mixtures".

Glebov et al., *International Chemical Engineering*, vol. 4, No. 4, pp. 613–617, "Methane pyrolysis reactor".

Dümbgen et al., *Chemie–Ing.–Techn.*, 40. Jahrgang, 1968, Heft 20, pp. 1004–1008, no translation.

*Ullmann's Enc. of Ind. Chem.*, 5th Edition, vol. A1, pp. 97–144.

*Primary Examiner*—Glenn Caldarola
*Assistant Examiner*—Thuan D. Dang
*Attorney, Agent, or Firm*—Keil & Weinkauf

[57] ABSTRACT

The invention relates to a process for the production of acetylene and synthesis gas by partial oxidation of hydrocarbons with oxygen, wherein the gaseous reactants are separately preheated, intimately mixed in a mixing zone, reacted after passing a burner block and rapidly quenched with an aqueous quench medium after reaction, further characterized in that the aqueous quench medium is recirculated in a closed system. Preferably the ratio of the gaseous reactants is selected in such a way that acetylene and soot produced in the reaction are obtained in a weight ratio of 50 to 500.

26 Claims, No Drawings

PROCESS FOR THE PRODUCTION OF ACETYLENE AND SYNTHESIS GAS

The present invention relates to a process for the production of acetylene and synthesis gas by partial oxidation of hydrocarbons with oxygen, characterized in that the gaseous reactants are separately preheated intensively mixed in the mixing zone, reacted after passing a burner block and rapidly quenched with an aqueous quench medium after the reaction.

The production of acetylene and synthesis gas by partial oxidation of hydrocarbons is well known. The partial oxidation of methane (natural gas) to form acetylene and synthesis gas is employed worldwide on a large scale. While the sole production of synthesis gas from natural gas by partial oxidation is a technically simple process the synthesis gas process coupled with the acetylene production is restricted to precise conditions of space, time and amounts used. Usually the reactants natural gas and oxygen are separately preheated to temperatures up to 700° C., intensively mixed in the mixing zone (diffuser) and brought to reaction after passing a burner block.

The burner block usually comprises a number of specifically shaped channels in which the velocity of the reactive oxygen/natural gas mixture is higher than the flame propagation speed so that the flame below the burner block cannot backfire into the diffuser where the pre-mixing takes place.

The reaction chamber adjacent to the burner block has a specific volume in order to allow the hot product gas to leave the reaction chamber within a few milliseconds so that the residence time of the acetylene containing reaction gases is very short. The extremely short residence time in combination with a low pressure leads to the partial oxidation of the hydrocarbon to acetylene and synthesis gas since in the short time the total conversion of the reactants to synthesis gas is not possible. After this time during which the reaction equilibria corresponding to the temperature level of 1500° to 2000° C. cannot be obtained the reaction products are almost instantaneously cooled or quenched to a temperature below 300° C. by using water or residue oils as quench media. The quenching ensures that the acetylene formed does not decompose into carbon and hydrogen or that the water formed during the reaction (process water) does not react with acetylene to form carbon monoxide and hydrogen. Normally these processes are performed at atmospheric pressure or slightly enhanced pressure. Apart from natural gas all gaseous or easily vaporizable hydrocarbons may be used under slightly changing the process conditions. Whereas the sole production of synthesis gas from natural gas by partial oxidation is a technically simple process in which nearly no side products are produced the synthesis gas process coupled with the production of acetylene always leads to formation of smaller or greater amounts of soot depending on the hydrocarbon used as a reactant. In contrast to the partial oxidation of methane to synthesis gas during which the formation of soot can nearly be suppressed by the application of high pressures and relatively long residence times in the process for the partial oxidation of hydrocarbons to acetylene and synthesis gas the low pressure and extremely short residence time of a few milliseconds are responsible for the production of acetylene, i.e. the incomplete conversion of the reactants to synthesis gas. Thus, the formation of soot cannot be prevented.

Furthermore, the concentration of the major constituents of the reacted or cracked gas depend on the oxygen/hydrocarbon ratio in the feed. With increasing oxygen supply the acetylene concentration increases until it passes a maximum. Usually the volume ratio (under standard temperature and pressure) of oxygen to natural gas is not more than approximately 0.6 in order to obtain a maximum concentration of acetylene. The rapid cooling of the cracked gas does not only lead to a removal of heat from the product gas mixture but also to a withdrawal of soot from the reaction products.

According to the state of the art the quenching may be performed by two processes, the water quench process and the oil quench process, respectively. (Ullmann's Encyclopedia of Industrial Chemistry, 5th Edition, Volume A1, pages 97–144).

In the water quench process the product gas is cooled to approximately 80° to 90° C. by the aqueous quench medium during quenching. The part of the soot formed during the reaction is removed from the product gas mixture by quenching. The product gas mixture is thereafter further purified and cooled by washing with recirculated water in a cooling column in which further parts of the soot are removed. Finally the gas mixture is passed through an electro filter in which further soot is removed and washed out with water. Thus, the water effluences from the quench system, the cooling column and the electro filter carry the washed-out soot. However, the water is not capable of dispersing or stably incorporating the high amounts of soot produced in the process. In order to avoid flow problems or problems associated with sticking of the soot contained in the water the soot has to be removed from the water. For this reason these combined water effluences are then passed to a soot decanter. In this decanter (basin decanter) the soot floats due to remaining gas attached to the soot. The upper soot layer contains 4 to 8 weight percent of carbon, depending on the feed stock. This soot is scraped off the water surface and subsequently degassed in vessels under stirring whereby a soot sludge is obtained with a water content of more than 90%. This soot sludge is incinerated in special incineration means. The combined water effluences are then passed from the basin decanters to cooling towers in which they are cooled and then recirculated to the quench, the cooling column and the electrofilter.

The water quench process leads to considerable energy losses by cooling the water in cooling towers and is associated with emission problems and problems due to the bad smell of the emissions. The soot foams are an important source for the emission of aromatics, especially benzene, when they are floating in open basin decanters. In the cooling towers hydrocarbon emissions from the water may occur as well.

A second process for the rapid cooling of the reaction products is the quenching with oils, for example residue oils or high boiling aromatic heavy oils. In using these oils for quenching or cooling the soot formed is suspended in the oil. The product gas leaves the burner with a temperature of 200° to 250° C. The heat absorbed by the quench medium can be transferred to water under production of steam by passing the oil through waste heat boilers before returning it to the quench. Thus, the energy losses in this process are smaller than in the water quench process. The remaining heat of the product gas is removed in closed system coolers. Hereby emissions are prevented. The cooled oil is recycled to the burner.

Whereas in the water quench process only the water losses in the decanter and cooling tower must be replaced in the oil quench process the addition of considerable amounts of oil is necessary. The reason for this lies in the fact that part of the oil is cracked in the quench during the contact with the reaction gas having a temperature of up to 2000° C. The oil is thus cracked and reacted to hydrogen, lighter aromatics and soot or coke. The carbon or soot formed in the reaction of the gases and in the cracking of the oil used for the quenching is suspended in the oil. Since the capability of the oil to incorporate carbon and soot and cracking products of the oils is limited, a part of the soot containing oil has to be regenerated, it has to be separated from the soot. This is accomplished for example by distilling the oil whereby the carbon is obtained in form of fine granules. The disadvantage of the oil quenching process is the technically expensive regeneration of the soot containing oils and the necessary addition of larger amounts of heavy oils. Furthermore, considerable amounts of soot or coke and lighter decomposition products of the heavy oils, so called pyrolysis oils are collected. The advantage of the oil quenching process is that it is free of emissions and involves only a small loss of process heat, see Ullmann's Encyclopedia of Industrial Chemistry, Fifth Edition, Volume A1, pages 106 to 115.

The problem underlying the present invention is to avoid the disadvantages of the water quench process and the oil quench process.

The problem is solved according to the present invention by the subject matter of the patent claims.

According to one embodiment of the present invention a process for the production of acetylene and synthesis gas by partial oxidation of hydrocarbons with oxygen is provided, wherein gaseous reactants are separately preheated, intensively mixed in a mixing zone, reacted after passing a burner block and rapidly quenched with an aqueous medium after reaction, and which is further characterized in that the aqueous quench medium is recirculated in a closed system.

It has been found that the amount of soot obtained in the production of acetylene and synthesis gas by partial oxidation of hydrocarbons with oxygen can be reduced to a large extent.

It also has been found that with increasing ratio of oxygen to hydrocarbon in the reactant gases the amount of soot obtained in the cracked gas can be reduced to a far greater extent than the amount of acetylene. Thus, by adjusting the oxygen/hydrocarbon-ratio the formation of soot in the production of acetylene can be suppressed to a large extent while the formation of acetylene is reduced only by small amounts.

In reducing the acetylene concentration in the cracked gas to half of its maximum value, i.e. by employing a half acetylene capacity of the burner (example 2), the soot formation amounts only to approximately 7 percent of the soot formation in the case the burner is operated at full acetylene capacity (comparative example 1) thus yielding a maximum acetylene yield.

When the oxygen to hydrocarbon ratio is increased in such a way that the acetylene capacity of the burner is reduced to one third of its maximum (example 3) the soot formation is reduced to approximately 2 percent of the soot formation at maximum acetylene capacity of the burner (comparative example 1).

The great reduction of the soot formation in comparison to the acetylene formation according to the present invention allows for a modification of the above mentioned water quenching process in such a way that closed systems for the quench and cooling water circulation may be provided. In the process according to the present invention the process heat of the quench with water can be carried off by suitable cooling systems, for example air coolers or plate coolers which may as well be applied in combination with cooling towers. A removal of the soot in open basin decanters and the necessary removal of heat in cooling towers can thus be avoided. Thereby the smell and emission problems may be removed which otherwise lead to environmental problems. The soot formed during the reaction is preferably taken up by the quench or cooling water and remains in the water. Thus the withdrawal and incineration of greater amounts of soot sludge or soot foam is obsolete. The soot is withdrawn from the recirculated quench of the cooling water preferably only in such amounts which correspond to the amounts of process water formed in the reaction which has to be withdrawn from the circulation. From this withdrawn relatively small amount of water the soot can be separated by any means.

According to another embodiment of the present invention, part of the aqueous quench medium, preferably at least in a quantity corresponding to at least the process water formed in the oxidation reaction, is removed from the circulation and optionally replaced by fresh aqueous medium. Thereby the amount of soot removed from the circulation and the amount remaining in the circulation may be adjusted.

The process according to the present invention thus combines the advantages of the quench process using oil, especially the recirculation in a closed system with those of the water quench process in which a cheap quench medium is used which is not consumed during the process and thus does not need to be added in a continuous manner. The disadvantages of the both known quench processes are avoided, especially those of the open basin decanters and cooling towers in the water quench process and those of the technically complicated regeneration of the soot containing oils and the necessity of continuously adding heavy oils in the oil quench process.

The hydrocarbons which can be employed according to the present invention may be any hydrocarbons which are sufficiently volatile. The hydrocarbons may contain only one type of hydrocarbons but may be as well mixtures of hydrocarbons.

According to one embodiment of the present invention natural gas is employed as hydrocarbon. Every natural gas composition may be employed. According to one embodiment of the present invention the natural gas contains at least 98 volume percent methane.

According to the present invention all lower hydrocarbons, especially the paraffin methane, ethane, propane and butane, either alone or mixtures thereof, may be employed in the present process.

According to another embodiment of the invention the gas may contain other gases besides the hydrocarbons, for example nitrogen, carbon dioxide, rare gases.

According to one embodiment of the present invention the gas employed may be pure butane.

The ratio of oxygen atoms in the oxygen and carbon atoms in the hydrocarbons may be adjusted according to the desired acetylene to soot weight ratio or the desired acetylene production. If a high acetylene production is desired the ratio of oxygen atoms in the oxygen to carbon atoms in the hydrocarbon may be lowered, whereas for a smaller acetylene production combined with a very high acetylene to soot weight ratio and a very small soot production this ratio may be higher. The process conditions may be varied according to the desired reaction products according to the present invention.

Preferably in the process according to the present invention the atomic ratio of oxygen atoms in the oxygen to carbon atoms in the hydrocarbons is at least 1.05, preferably the atomic ratio is from 1.15 to 1.4.

According to one embodiment of the present invention the hydrocarbons used are natural gas and the standard volume ratio of oxygen to the natural gas is above 0.6, preferably in the range from 0.61 to 0.78, preferably from 0.625 to 0.7.

According to one embodiment of the present invention the ratio of the gaseous reactants is selected in such a way obtained from the quench and cooling water which was removed from the closed quench or cooling water circuit. In the process according to the comparative examples the soot was removed by the decanting process from the quench and cooling water as it is described above.

The exact experimental conditions and results of the experiments are summarized in the following table:

|  | Example | | | | | | |
| --- | --- | --- | --- | --- | --- | --- | --- |
|  | Comparative Example 1 | Example 2 | 1 | 2 | 3 | 4 | 5 |
| Natural Gas Feed $Nm^3/h$ | 7.200 | 6.900 | 6.500 | 6.350 | 6.000 | 5.875 | 5.600 |
| Oxygen Feed $Nm^3/h$ | 4.200 | 4.200 | 4.200 | 4.200 | 4.200 | 4.200 | 4.200 |
| Oxygen/Natural Gas Volume Ratio | 0.583 | 0.609 | 0.646 | 0.661 | 0.7 | 0.715 | 0.75 |
| O/C Ratio* | 1.166 | 1.218 | 1.292 | 1.322 | 1.4 | 1.43 | 1.5 |
| Cracked Gas $Nm^3/h$ | 13.800 | 13.800 | 13.800 | 13.800 | 13.800 | 13.800 | 13.800 |
| Acetylene, % by volume | 8.5 | 7.8 | 6.4 | 4.5 | 2.8 | 2.5 | 1.6 |
| Acetylene Production, t per day | 33 | 30 | 25 | 17 | 11 | 10 | 6 |
| Synthesis Gas $Nm^3$ per day | 300.000 | 305.Q00 | 310.000 | 315.000 | 321.000 | 322.000 | 325.000 |
| Process Water, $m^3$ per day | 86 | 80 | 67 | 62 | 58 | 55 | 50 |
| Soot Production, kg/h | 75 | 55 | 10 | 5 | 1.6 | 1.2 | 0.6 |
| Soot sludge (90% water), kg per day | 18.000 | 13200 | 2.400 | 1.200 | 385 | 288 | 144 |
| Soot water circuit, % soot by weight** | <2.1> | <1.65> | 0.36 | 0.19 | 0.07 | 0.07 | 0.03 |
| Acetylene to soot weight ratio | 18 | 22 | 104 | 142 | 287 | 347 | 417 |
| Natural Gas Feed $Nm^3/h$ | 7.200 | 6.900 | 6.500 | 6.350 | 6.000 | 5.875 | 5.600 |
| Synthesis Gas Analysis, % by volume | | | | | | | |
| Carbonmonoxide | 283 | 28.6 | 30.5 | 32.8 | 33.8 | 34 | 34.2 |
| Hydrogen | 61 | 61.3 | 61.8 | 62.2 | 62.4 | 62.5 | 62.5 |
| Methane, carbondioxide and others | 10.4 | 9.9 | 7.6 | 4.9 | 3.8 | 3.5 | 3.3 |
| Oxygen | 0.3 | 0.2 | 0.1 | <0.1 | 0.02 | 0.01 | <0.01 |

*ratio of oxygen atoms in the oxygen to carbon atoms in the natural gas
**in the removed quench water that acetylene and soot produced in the reaction are obtained in a weight ratio of 50 to 500, preferably in a weight ratio of 50 to 150.

According to one embodiment of the present invention the soot concentration in the acqueous quench medium is not more than 1% by weight, preferably from 0.1 to 1% by weight, preferably from 0.2 to 0.4% by weight. Preferably the volume ratio of oxygen to natural gas is around 0.646, the ratio of oxygen atoms in the oxygen to carbon atoms in the hydrocarbons is approximately 1.3, thus yielding a acetylene to soot weight ratio of approximately 100.

Further features and advantages of the invention are apparent from the following examples.

The examples were carried out using an apparatus as it is described in Ullmann's Encyclopedia of Industrial Chemistry, 5th Edition, Volume 1, 1985, page 107. Reactant gases were natural gas and oxygen. The natural gas contained at least 98 volume percent methane.

However, every natural gas composition or gas mixture may be employed according to the present invention.

The reactant gases were separately heated to 600° C., intimately mixed in the mixing zone of the burner and brought to reaction after passing through a diffuser and the burner block. After a reaction time of a few milliseconds the acetylene containing cracked crack gases were quenched with water to a temperature of 80° C. The products acetylene and synthesis gas were obtained in a normal manner by fractionated absorption and subsequent desorption with aid of a suitable solvent. The soot formed as a by-product was From the above examples it can be taken that in the process according to comparative example 1 a soot concentration of 2.1% in the process water is obtained when the soot is removed together with the process water. In this process due to the high soot concentration the unfavorable and environmentally critical decanting process must be applied to remove the soot from the quench and cooling water. Furthermore cooling of the water in cooling towers is necessary. The same applies for comparative example 2, where a soot concentration of 1.65% is obtained. The soot concentration is too high for a recirculation of the quench medium. According to examples 1 and 3 the soot concentrations are reduced to 0.36% down to 0.07%, respectively. These soot concentrations do not pose any problems in recycling the quench and cooling water in a closed system. The removal of soot by the removal of process water formed in the reaction process is sufficient to maintain a soot concentration in the water which does not interfere with the quench and cooling water circulation. Therefore, it was possible to employ the closed system for the quench and cooling water circulation in examples 1 to 3. Approximately 3 $m^3$ of process water containing soot need to be removed per hour. The removed water may for example be filtered to remove the soot or may be fed to a sewage purification plant. In example 1 the production of acetylene is three quarter of the production in comparative example 1. The soot production, however, is reduced from 75 kg/hr to 10 kg/hr, thus by a factor of nearly 8 (the soot production according to example 1 is about ⅛ of the soot production according to comparative example 1).

In example 2 the acetylene production is reduced to ½ of the production of comparative example 1. The soot production, however, is reduced by a factor of 15 to 5 kg/hr in comparison to comparative example 1.

Examples 4 and 5 show results for an even higher oxygen to natural gas ratio. Soot concentrations in the circuit water amount to 0.07 and 0.03 weight percent, respectively. The acetylene production decreases to 10 and 6 tons per day, respectively. At the same time the acetylene to soot weight ratio increases to 347 and 417 respectively. Thus, if according to one embodiment of the invention reduced acetylene yields can be tolerated the soot production may be reduced to very small amounts, thus giving very high acetylene to soot weight ratios. The oxygen to natural gas ratio employed may thus according to one embodiment of the present invention depend on the desired amounts and types of reaction products and the required reduction of the amount of soot formed in the reaction.

The composition of the hydrocarbon gas may be varied. In the following example (example 6) the hydrocarbon feed had the following composition: methane 86 volume %, ethane 0.5 volume %, propane 2.7 volume %, butanes 9.6 volume %, pentanes 0.1%, the remainder being nitrogen, carbon dioxide and helium. This hydrocarbon mixture has a carbon atom concentration of 1.3428 $Nm^3$ $C/Nm^3$ of the mixture. The following results were obtained:

TABLE I

| | |
|---|---|
| Example 6 Gas Feed, $Nm^3h$ | 5.150 |
| Oxygen Feed, $Nm^3h$ | 4.200 |
| Oxygen/Hydrocarbon Volume Ratio | 0.816 |
| O/C- Ratio | 1.215 |
| Cracked Gas $Nm^3h$ | 12,400 |
| Acetylene, Percent by Volume | 6,79 |
| Acetylene Production, t per day | 23.5 |
| Synthesis Gas, $Nm^3$ per day | 276,500 |
| Process Water; $Nm^3$ per day | 58 |
| Soot Production, kg/h | 15 |
| Soot Water Circuit, % soot by weight in the removed quench water | 0.62 |
| Synthesis Gas analysis % by volume | Carbon monoxide 34.7 |
| | Hydrogen 59.1 |
| | Methane, Carbon Dioxi- and others 6.1 |
| | Oxygen 0.1 |
| Acetylene to Soot Weight Ratio | 65 |

This example demonstrates that the composition of the hydrocarbons employed may be varied according to the present invention. The amount of soot formed was still low enough for employing a closed quench and cooling water system.

EXAMPLE 7

In this example pure butane was employed.

Butane feed, $Nm^3/h$ 1930 (5000 kg)

Oxygen feed, $Nm^3/h$ 4200

Oxygen/butane volume ratio 2,176

O/C-Ratio 1.088

Acetylene % by volume 6,85

Acetylene production, t per day 31.5

Examples 3–6 present more experimental results showing that the soot formation decreases much more rapidly than the acetylene production when the ratio of oxygen to natural gas is increased.

The experimental results show that according to the present invention the soot formation in the process for the production of acetylene and synthesis gas by partial oxidation of hydrocarbons with oxygen can be reduced in such a way that the aqueous quench medium employed in the process may be recirculated in a closed system.

We claim:

1. A process for the production of acetylene and synthesis gas by partial oxidation of hydrocarbons with oxygen, which process comprises separately preheating gaseous reactants comprising hydrocarbons and oxygen, wherein the atomic ratio of oxygen atoms in the oxygen to carbon atoms in the hydrocarbons is at least 1.05, intimately mixing the separately preheated gaseous reactants in a mixing zone, reacting the intimately mixed gaseous reactants after passing a burner block whereby less than the full acetylene capacity of the burner block is employed, rapidly quenching with aqueous quench medium after reaction, and recirculating the aqueous quench medium in a closed system.

2. The process defined in claim 1, further comprising indirectly cooling the aqueous quench medium.

3. The process defined in claim 1, further comprising removing part of the aqueous quench medium in a quantity corresponding to at least what process water is formed in the oxidation reaction from re-circulation in the closed system, and optionally replacing what aqueous quench medium is removed with fresh aqueous medium.

4. The process defined in claim 3, further comprising separating from that part of the aqueous quench medium which is removed from re-circulation any soot formed in the reaction and contained in the aqueous quench medium after quenching.

5. The process defined in claim 1, characterized in that the atomic ratio is from 1.05 to 1.60.

6. The process defined in claim 1 characterized in that the hydrocarbons used are natural gas and the standard volume ratio of oxygen to the natural gas is above 0.6.

7. The process defined in claim 6, characterized in that the standard volume ratio is from 0.61 to 0.78.

8. The process defined in claim 6, characterized in that the standard volume ratio is from 0.625 to 0.70.

9. The process defined in claim 1 characterized in that the soot concentration in the aqueous quench medium is not more than 1 percent by weight.

10. The process defined in claim 1, characterized in that the atomic ratio is from 1.15 to 1.40.

11. The process defined in claim 1 characterized in that the soot concentration in the aqueous quench medium is from 0.1 to 1 percent by weight.

12. The process defined in claim 1 characterized in that the soot concentration in the aqueous quench medium is from 0.2 to 0.4 percent by weight.

13. A process for the production of acetylene and synthesis gas by partial oxidation of hydrocarbons with oxygen which process comprises separately preheating gaseous reactants, intimately mixing the separately preheated gaseous reactants in a mixing zone, reacting the intimately mixed gaseous reactants after passing a burner block whereby less than the full acetylene capacity of the burner block is employed, rapidly quenching with an aqueous quench medium after reaction, recirculating the aqueous quench medium in a closed system, and selecting the composition of the gaseous reactants so that acetylene and soot produced in the reaction are obtained in a weight ratio of 50 to 500.

14. The process defined in claim 13 characterized in that acetylene and soot produced in the reaction are obtained in a weight ratio of 50 to 150.

15. The process defined in claim 13 characterized in that in the gaseous reactants the atomic ratio of oxygen atoms in the oxygen to carbon atoms in the hydrocarbons is at least 1.05.

16. The process defined in claim 15 characterized in that the atomic ratio is from 1.05 to 1.60.

17. The process defined in claim 15 characterized in that the hydrocarbons used are natural gas and the standard volume ratio of oxygen to the natural gas is above 0.6.

18. The process defined in claim 15, characterized in that the standard volume ratio is from 0.61 to 0.78.

19. The process defined in claim 15 characterized in that the atomic ratio is from 1.15 to 1.40.

20. The process defined in claim 15, characterized in that the standard volume ratio is from 0.625 to 0.70.

21. The process defined in claim 13 further comprising indirectly cooling the aqueous quench medium.

22. The process defined in claim 13 characterized in that water in a quantity corresponding to the process water formed in the oxidation reaction is removed from the circulation.

23. The process defined in claim 13 further comprising separating from that part of the aqueous quench medium which is removed from re-circulation any soot formed in the reaction and contained in the aqueous quench medium after quenching.

24. The process defined in claim 13 characterized in that the soot concentration in the aqueous quench medium is not more than 1 percent by weight.

25. The process defined in claim 13 characterized in that the soot concentration in the aqueous quench medium is from 0.1 to 1 percent by weight.

26. The process defined in claim 13 characterized in that the soot concentration in the aqueous quench medium is from 0.2 to 0.4 percent by weight.

* * * * *